US012428434B2

(12) United States Patent
Ye et al.

(10) Patent No.: US 12,428,434 B2
(45) Date of Patent: Sep. 30, 2025

(54) ALKALI METAL MONOHYDROGEN CYANURATE COMPOUND, CRYSTAL THEREOF, PREPARATION METHOD THEREFOR AND USE THEREOF

(71) Applicants: FUJIAN INSTITUTE OF RESEARCH ON THE STRUCTURE OF MATTER, CHINESE ACADEMY OF SCIENCES, Fujian (CN); MINDU INNOVATION LABORATORY, Fujian (CN)

(72) Inventors: Ning Ye, Fujian (CN); Donghong Lin, Fujian (CN); Min Luo, Fujian (CN)

(73) Assignees: FUJIAN INSTITUTE OF RESEARCH ON THE STRUCTURE OF MATTER, CHINESE ACADEMY OF SCIENCES, Fujian (CN); MINDU INNOVATION LABORATORY, Fujian (CN)

( * ) Notice: Subject to any disclaimer, the term of this patent is extended or adjusted under 35 U.S.C. 154(b) by 1157 days.

(21) Appl. No.: 17/263,658

(22) PCT Filed: Aug. 1, 2018

(86) PCT No.: PCT/CN2018/098122
§ 371 (c)(1),
(2) Date: Jan. 27, 2021

(87) PCT Pub. No.: WO2020/024179
PCT Pub. Date: Feb. 6, 2020

(65) Prior Publication Data
US 2021/0309673 A1    Oct. 7, 2021

(51) Int. Cl.
| C07D 251/32 | (2006.01) |
| C07F 1/02 | (2006.01) |
| C07F 1/04 | (2006.01) |
| G02F 1/355 | (2006.01) |
| G02F 1/35 | (2006.01) |
| G02F 1/37 | (2006.01) |
| G02F 1/39 | (2006.01) |

(52) U.S. Cl.
CPC ............. *C07F 1/02* (2013.01); *C07D 251/32* (2013.01); *C07F 1/04* (2013.01); *G02F 1/3551* (2013.01); *G02F 1/354* (2021.01); *G02F 1/37* (2013.01); *G02F 1/392* (2021.01)

(58) Field of Classification Search
CPC .................................................. C07D 251/32
See application file for complete search history.

(56) References Cited

U.S. PATENT DOCUMENTS

| 3,501,468 A | 3/1970 | Moore et al. |
| 2007/0032649 A1 | 2/2007 | Stephan et al. |

FOREIGN PATENT DOCUMENTS

| JP | S5818370 A | 2/1983 |
| SU | 906992 A1 | 2/1982 |
| WO | 2014179353 A1 | 11/2014 |

OTHER PUBLICATIONS

American Chemical Society. Chemical Abstract Service. CAS RN 2275772-37-5. Entered into STN: Mar. 1, 2019. (Year: 2019).*
American Chemical Society. Chemical Abstract Service. RN 26572-48-5. First entered into STN: Nov. 16, 1984. (Year: 1984).*
American Chemical Society. Chemical Abstract Service. RN 36452-21-8. Entered into STN: Nov. 16, 1984. (Year: 1984).*
Nachbaur, E. et al.; "Formation and thermolysis of lithium cyanurates. Simple preparation of anhydrous lithium cyanate"; Monatsh. Chem.; vol. 104; Year: 1973; pp. 538-544.
Nichol, G. S. et al.; "Stoichiometry-dependent structures: an X-ray and neutron single-crystal diffraction study of the effect of reaction stoichiometry on the crystalline products formed in the potassium-cyanurate system"; Acta Crystal lographica, Section B: Structural Science; vol. B62; Year: 2006; ISSN 0108-7681; pp. 798-807.
Eliseev, A. A. et al.; "X-ray diffraction analysis of alkali metal cyanurates", Russian Journal of inorganic Chemstry; vol. 29, No. 9; Year: 1984; pp. 1387-1388.
Shao, Shibao et al.; Crystal Structure of Nickel Cyanurate; Chinese Journal of Structural Chemistry; vol. 15, No. 3, May 31, 1996, pp. 246-248.

* cited by examiner

*Primary Examiner* — John S Kenyon
(74) *Attorney, Agent, or Firm* — NKL Law; Allen Xue

(57) ABSTRACT

An alkali metal monohydrogen cyanurate compound of the chemical formula $AM(HC_3N_3O_3) \cdot nH_2O$ (specifically such as $KLi(HC_3N_3O_3) \cdot 2H_2O$, $RbLi(HC_3N_3O_3) \cdot 2H_2O$, $RbNa(HC_3N_3O_3) \cdot 2H_2O$) and a nonlinear optical crystal thereof are related to optoelectronic functional materials. Measured using a powder frequency doubling test method, and the powder frequency doubling effect of the nonlinear optical crystal is about 2-3 times that of $KH_2PO_4$ (KDP). The ultraviolet absorption edge of the nonlinear optical crystal is shorter than 250 nm. The nonlinear optical crystal can achieve the harmonic generator of double, triple, or quadruple frequency for Nd: YAG ($\lambda$=1.064 μm). Moreover, the nonlinear optical crystal is of a single crystalline structure, is colorless and transparent, and does not deliquesce in air.

19 Claims, 3 Drawing Sheets

ALKALI METAL MONOHYDROGEN CYANURATE COMPOUND, CRYSTAL THEREOF, PREPARATION METHOD THEREFOR AND USE THEREOF

TECHNICAL FIELD

The present invention belongs to the technical field of optoelectronic functional materials, and specifically relates to an alkali metal monohydrogen cyanurate compound, crystal thereof, preparation method therefor and use thereof.

BACKGROUND

Nonlinear optical effect of crystals refers to such an effect: when a laser beam with a certain polarization direction passes through a nonlinear optical crystal (such as a borate-based nonlinear optical crystal) in a certain incident direction, the frequency of the beam will change.

Crystals with nonlinear optical effects are called nonlinear optical crystals. The use of nonlinear optical crystals for laser frequency conversion broadens the range of laser wavelength and makes laser applications more extensive. Especially borate-based nonlinear optical crystals such as $BaB_2O_4$ (BBO), $LiB_3O_5$ (LBO), $KBe_2BO_3F_2$ (KBBF), $Sr_2Be_2B_2O_7$ (SBBO), $Ba_2Be_2B_2O_7$ (TBO), $K_2Al_2B_2O_7$ (KABO), $BaAl_2B_2O_7$ (BABO) and other crystals have attracted much attention due to their excellent optical properties. The development of optical photography, photolithography, precision instrument processing and other fields increasingly requires ultraviolet and deep ultraviolet laser coherent light sources, that is, ultraviolet and deep ultraviolet nonlinear optical crystals with excellent performance.

The basic structural element of BBO crystal is $(B_3O_6)^{3-}$ planar group. This group has a large conjugated π bond, making the ultraviolet absorption edge of BBO of around 189 nm, which limits the application of the crystal in the ultraviolet region. And, a large conjugated π bond may also cause a larger birefringence (Δn=0.12), which thereby limits its harmonic conversion efficiency and the quality of harmonic light.

The basic structural element of KBBF is $(BO_3)^{3-}$ planar group. This crystal has an ultraviolet absorption edge of about 155 nm, and has a moderate birefringence (Δn=0.07), which can achieve a wide phase matching range. It is by far the best deep ultraviolet nonlinear optical crystal. However, because KBBF is a layered crystal, and the layers are connected by electrostatic attraction rather than by valence bonds, the layered habit is serious, the growth rate in the z direction is very slow, the grown single crystal has obvious delamination, and the crystal is not easy to grow.

The basic structural element of SBBO is also $(BO_3)^{3-}$ planar group, but fluoride ions therein are replaced with oxygen, so that layers are connected to each other through oxygen bridges, thereby improving the layered habit of KBBF, while the structure of each layer remains basically unchanged. SBBO not only has a large macroscopic frequency doubling coefficient, low UV absorption edge (165 nm), and moderate birefringence (Δn=0.06), but also completely overcomes the layered habit of crystal and solves the problem of crystal growth. On this basis, a series of nonlinear optical crystals such as TBO, KABO and BABO are successively developed, which are collectively referred to as SBBO family crystals, by replacing the cation $Sr^{2+}$ and Be atoms, while keeping the structural conditions of the $(BO_3)^{3-}$ group basically unchanged. They overcome the layered habit of KBBF single crystal growth, but these crystals have not been able to replace KBBF single crystal so far, because the structural integrity of TBO crystals is not good, and the optical uniformity shown by their macroscopic properties is very poor, so that they cannot be used in practical devices. KABO and BABO crystals have good structural integrity and good optical uniformity. However, due to replacing Be with Al, the absorption edges of KABO and BABO crystals are red shifted to about 180 nm, so they are difficult to be used for deep ultraviolet harmonic output.

The basic structural element of LBO is to change one B atom of $(B_3O_6)^{3-}$ group from three coordination to four coordination, thus forming $(B_3O_7)^{5-}$ group. It has a large frequency doubling coefficient, and an ultraviolet absorption edge of about 160 nm. However, due to the fact that the $(B_3O_7)^{5-}$ groups in the actual crystal are interconnected and form helical chains at 45° to the Z-axis in space and cannot be arranged in parallel in the lattice, the birefringence of the crystal is too low (Δn=0.04-0.05), which seriously limits the phase matching range of the crystal in the ultraviolet region, and makes the advantage of the wide band gap not fully exerted.

Therefore, the development of ultraviolet and deep ultraviolet nonlinear optical crystal materials with excellent performance in all aspects has become one of the difficulties and frontiers in the current research field of nonlinear optical materials.

SUMMARY OF THE INVENTION

In order to overcome the shortcomings of the prior art, the present invention provides an alkali metal monohydrogen cyanurate compound of the chemical formula $AM(HC_3N_3O_3)\cdot_nH_2O$, wherein A and M are, the same or different, independently selected from alkali metals, for example Li, Na, K, Rb, Cs, Fr; n is selected from an integer of 0 or more.

Preferably, n is an integer selected from 0-10, such as 0, 1, 2, 3, 4, 5, 6, 7, 8, 9, 10, preferably 2.

According to an embodiment of the present invention, the compound may be selected from potassium lithium monohydrogen cyanurate dihydrate (chemical formula: $KLi(HC_3N_3O_3)\cdot 2H_2O$; referred to as KLHCY), rubidium lithium monohydrogen cyanurate dihydrate (chemical formula: $RbLi(HC_3N_3O_3)\cdot 2H_2O$; referred to as RLHCY), rubidium sodium monohydrogen cyanurate dihydrate (chemical formula: $RbNa(HC_3N_3O_3)\cdot 2H_2O$; referred to as RNHCY).

According to the present invention, the compound may be in the form of a nonlinear optical crystal.

The present invention also provides a nonlinear optical crystal of potassium lithium monohydrogen cyanurate dihydrate, the chemical formula of which is $KLi(HC_3N_3O_3)\cdot 2H_2O$.

According to the present invention, the nonlinear optical crystal of potassium lithium monohydrogen cyanurate dihydrate has an X-ray powder diffraction pattern substantially as shown in FIG. 3.

According to the present invention, the nonlinear optical crystal of potassium lithium monohydrogen cyanurate dihydrate does not have a symmetry center, and belongs to an orthorhombic crystal system, with the space group Pna2(1), the cell parameters a=15.387(6) Å, b=3.6524(16) Å, c=12.755(6) Å, α=β=γ=90°, Z=4, and the unit cell volume V=716.82 Å³.

The present invention also provides a nonlinear optical crystal of rubidium lithium monohydrogen cyanurate dihydrate, the chemical formula of which is $RbLi(HC_3N_3O_3)\cdot 2H_2O$.

According to the present invention, the nonlinear optical crystal of rubidium lithium monohydrogen cyanurate dihydrate has an X-ray powder diffraction pattern substantially as shown in FIG. 4.

According to the present invention, the nonlinear optical crystal of rubidium lithium monohydrogen cyanurate dihydrate does not have a symmetry center, and belongs to an orthorhombic crystal system, with the space group Pna2(1), the cell parameters $\alpha=15.682(7)$ Å, $b=3.7453(17)$ Å, $c=12.768(6)$ Å, $\alpha=\gamma=90°$, $Z=4$, and the unit cell volume $V=749.9$ Å$^3$.

The present invention also provides a nonlinear optical crystal of rubidium sodium monohydrogen cyanurate dihydrate, the chemical formula of which is $RbNa(HC_3N_3O_3)\cdot 2H_2O$.

According to the present invention, the nonlinear optical crystal of rubidium sodium monohydrogen cyanurate dihydrate has an X-ray powder diffraction pattern substantially as shown in FIG. 5.

According to the present invention, the nonlinear optical crystal of rubidium sodium monohydrogen cyanurate dihydrate does not have a symmetry center, and belongs to an orthorhombic crystal system, with the space group Pna2(1), the unit cell parameters $\alpha=15.829(18)$ Å, $b=3.964(5)$ Å, $c=13.068(16)$ Å, $\alpha=\gamma=90°$, $Z=4$, and the unit cell volume $V=819.8$ Å$^3$.

The present invention also provides a method for preparing the above-mentioned alkali metal monohydrogen cyanurate compounds, which includes reacting $AOH\cdot xH_2O$, $MOH\cdot yH_2O$ with $H_3C_3N_3O_3$ to obtain the alkali metal monohydrogen cyanurate compound; wherein A and M have the definitions given above; x and y are, the same or different, independently selected from an integer of 0 or more.

Preferably, x and y are, the same or different, independently an integer selected from 0-10, such as 0, 1, 2, 3, 4, 5, 6, 7, 8, 9, 10, preferably 0, 1.

According to the present invention, the molar ratio of the $AOH\cdot xH_2O$, $MOH\cdot yH_2O$ and $H_3C_3N_3O_3$ may be (0.5-2.5):(0.5-2.5):1, preferably (0.8-1.2):(0.8-1.2):1, such as 1:1:1.

The reaction can be carried out in a solvent, and the solvent may be selected from an organic solvent or an inorganic solvent, preferably an inorganic solvent, such as water;

The ratio of the total mass of raw materials to the solvent may be 5-50 g raw materials/100 ml solvent, preferably 10-30 g raw materials/100 ml solvent;

The temperature of the reaction may be 50-110° C., preferably 60-100° C., such as 80° C.;

According to the present invention, after the reaction is ended, the reaction liquid may be cooled at a constant cooling rate; after cooling, the above-mentioned alkali metal monohydrogen cyanurate compound can be obtained by washing with the solvent;

According to the present invention, the cooling rate is 1-10° C./hour, preferably 1-5° C./hour, such as 1° C./hour, 5° C./hour;

According to the present invention, the reaction liquid is cooled to 0-40° C., preferably 10-40° C., such as 10° C., 40° C.;

The solvent used for the washing is water, acetone or a mixture thereof, and the above-mentioned solvent can be used for washing several times; preferably, the solvent used for the washing is acetone.

According to the present invention, a crystal is prepared by the above method, and the volume of the crystal is greater than 2.0 mm$^3$.

The present invention also provides use of the above-mentioned alkali metal monohydrogen cyanurate compound (such as crystal), which can be used for frequency conversion of laser output, harmonic generator in ultraviolet region, optical parametric amplifier and optical waveguide device;

Preferably, the compound can achieve a harmonic light output of double, triple, quadruple, quintuple or sextuple frequency for a laser beam with a wavelength of 1.064 m;

Preferably, the compound can be used for optical parametric amplifiers from infrared to ultraviolet region.

Beneficial Effects of the Present Invention

The present invention provides an alkali metal monohydrogen cyanurate compound of the chemical formula $AM(HC_3N_3O_3)\cdot nH_2O$ (specifically such as $KLi(HC_3N_3O_3)\cdot 2H_2O$, $RbLi(HC_3N_3O_3)\cdot 2H_2O$, $RbNa(HC_3N_3O_3)\cdot 2H_2O$) and its nonlinear optical crystal; the nonlinear optical crystal has an extremely strong phase matching capability (measured using a powder frequency doubling test method, and the powder frequency doubling effect thereof is about 2-3 times that of $KH_2PO_4$ (KDP)); and the ultraviolet absorption edge thereof is shorter than 250 nm. In addition, the nonlinear optical crystal can achieve the harmonic generator of double, triple, or quadruple frequency for Nd:YAG ($\lambda=1.064$ μm). Moreover, the nonlinear optical crystal is of a single crystalline structure, is colourless and transparent, and does not deliquesce in air. It is thus expectable that $AM(HC_3N_3O_3)\cdot nH_2O$ (specifically such as $KLi(HC_3N_3O_3)\cdot 2H_2O$, $RbLi(HC_3N_3O_3)\cdot 2H_2O$, $RbNa(HC_3N_3O_3)\cdot 2H_2O$) will be widely used in a variety of nonlinear optical fields, and will develop the nonlinear optical application of ultraviolet wavelength bands.

SPECIFIC MODE FOR CARRYING OUT THE INVENTION

Figure 1:
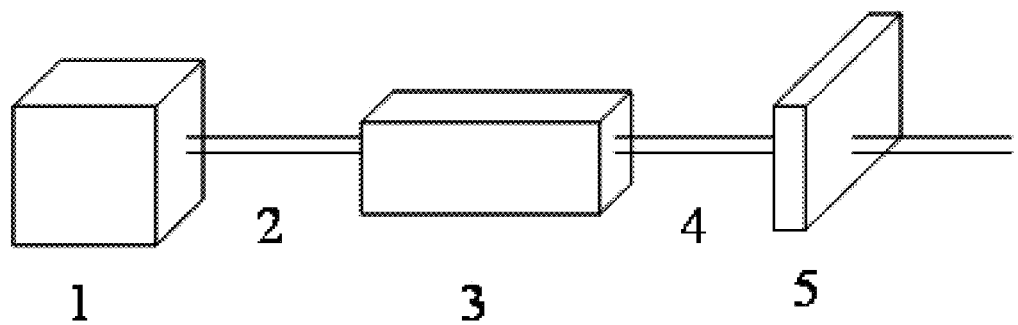
FIG. 1 is a typical schematic diagram of nonlinear optical effects when KLHCY, RLHCY, RNHCY crystals are used as frequency doubling crystals, where 1 is a laser, 2 is an incident laser beam, 3 is a single crystal after crystal post-processing and optical processing, 4 is an output laser beam, 5 is a filter.
Figure 2:
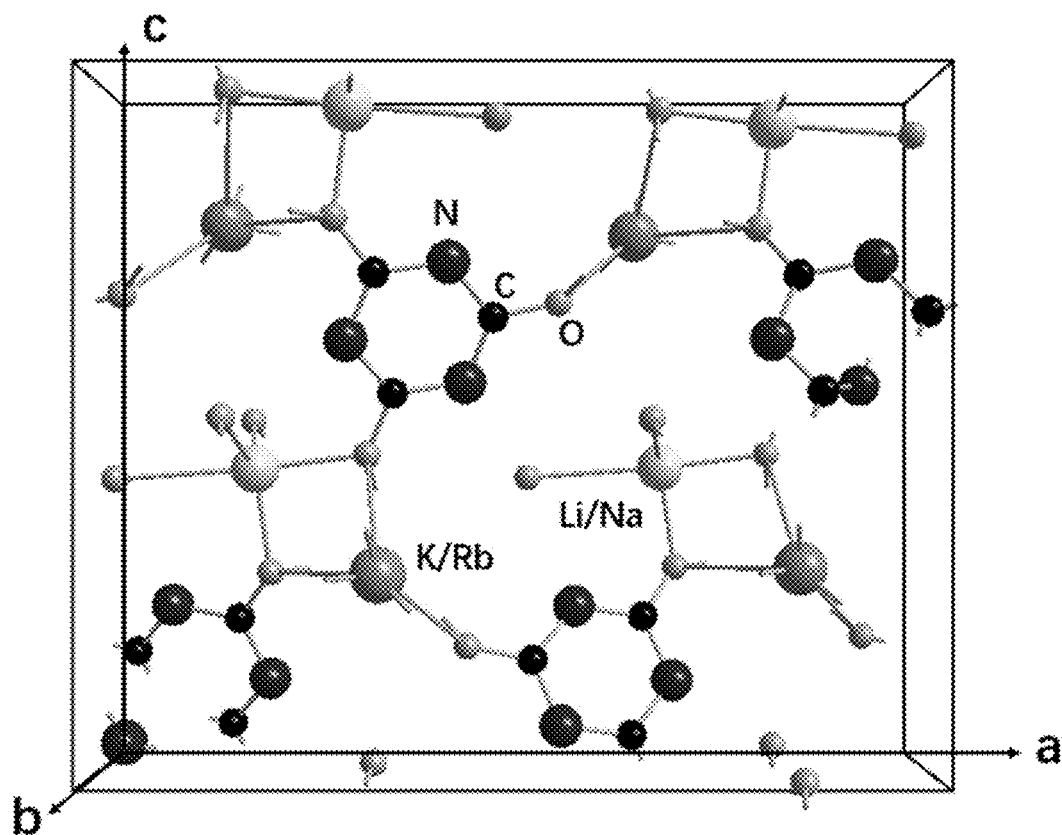
FIG. 2 is a schematic diagram of the structures of KLHCY, RLHCY, RNHCY crystals (KLHCY, RLHCY, RNHCY are isomorphic compounds).

As mentioned above, the present invention provides a compound with a new structure and its crystal, the structural formula of which is $AM(HC_3N_3O_3)\cdot nH_2O$ (specifically such as KLHCY, RLHCY, RNHCY), in which monohydrogen cyanurate radical provides excellent aqueous solution growth performance and nonlinear performance for crystal growth.

The technical solution of the present invention will be further described in detail with reference to specific embodiments. It is to be understood that the following examples are only illustrative and explanatory of the present invention and should not be construed as limiting the scope of the present invention. All the techniques realized based on the above-mentioned contents of the present invention are covered in the protection scope of the present invention.

Unless otherwise specified, the raw materials and reagents used in the following examples are all commercially available products, or can be prepared by known methods.

EXAMPLE 1

Preparation of $KLi(HC_3N_3O_3)\cdot 2H_2O$, $RbLi(HC_3N_3O_3)\cdot 2H_2O$ and $RbNa(HC_3N_3O_3)\cdot 2H_2O$ Single Crystals by Aqueous Solution Method Raw materials used for the preparation of $KLi(HC_3N_3O_3)\cdot 2H_2O$ single crystal:
  KOH 3.44 g (0.06 mol)
  $LiOH\cdot H_2O$ 2.60 g (0.06 mol)
  $H_3C_3N_3O_3$ 7.74 g (0.06 mol)
  $H_2O$ 50 ml The specific operation steps were as follows: the above raw materials weighed according to the above amounts were put into a 100 ml beaker, to which was put a magnetic bar; the beaker was placed on a magnetic heating stirrer; the beaker was heated to 80° C. with stirring, and then cooled to 40° C. at a cooling rate of 5° C./hour. After cooling, the sample was washed with acetone to obtain $KLi(HC_3N_3O_3)\cdot 2H_2O$ single crystal with a size of 5×1×1 mm.

Raw materials used for the preparation of $RbLi(HC_3N_3O_3)\cdot 2H_2O$ single crystal:
  $RbOH\cdot H_2O$ 7.23 g (0.06 mol)
  $LiOH\cdot H_2O$ 2.60 g (0.06 mol)
  $H_3C_3N_3O_3$ 7.74 g (0.06 mol)
  $H_2O$ 50 ml The specific operation steps were as follows: the above raw materials weighed according to the above amounts were put into a 100 ml beaker, to which was put a magnetic bar; the beaker was placed on a magnetic heating stirrer; the beaker was heated to 80° C. with stirring, and then cooled to 40° C. at a cooling rate of 5° C./hour. After cooling, the sample was washed with acetone to obtain $RbLi(HC_3N_3O_3)\cdot 2H_2O$ single crystal with a size of 1×1×5 mm.

Raw materials used for the preparation of $RbNa(HC_3N_3O_3)\cdot 2H_2O$ single crystal:
  NaOH 2.40 g (0.06 mol)
  $RbOH\cdot H_2O$ 7.23 g (0.06 mol)
  $H_3C_3N_3O_3$ 7.74 g (0.06 mol)
  $H_2O$ 50 ml The specific operation steps were as follows: the above raw materials weighed according to the above amounts were put into a 100 ml beaker, to which was put a magnetic bar; the beaker was placed on a magnetic heating stirrer; the beaker was heated to 80° C. with stirring, and then cooled to 10° C. at a cooling rate of 5° C./hour. After cooling, the sample was washed with acetone to obtain $RbNa(HC_3N_3O_3)\cdot 2H_2O$ single crystal with a size of 1×5×1 mm.

EXAMPLE 2

Preparation of $KLi(HC_3N_3O_3)\cdot 2H_2O$, $RbLi(HC_3N_3O_3)\cdot 2H_2O$ and $RbNa(HC_3N_3O_3)\cdot 2H_2O$ Single Crystals by Aqueous Solution Method Raw materials used for the preparation of $KLi(HC_3N_3O_3)\cdot 2H_2O$ single crystal:
  KOH 3.44 g (0.06 mol)
  $LiOH\cdot H_2O$ 2.60 g (0.06 mol)
  $H_3C_3N_3O_3$ 7.74 g (0.06 mol)
  $H_2O$ 50 ml The specific operation steps were as follows: the above raw materials weighed according to the above amounts were put into a 100 ml beaker, to which was put a magnetic bar; the beaker was placed on a magnetic heating stirrer; the beaker was heated to 80° C. with stirring, and then cooled to 40° C. at a cooling rate of 1° C./hour. After cooling, the sample was washed with acetone to obtain $KLi(HC_3N_3O_3)\cdot 2H_2O$ single crystal with a size of 5×2×2 mm.

Raw materials used for the preparation of $RbLi(HC_3N_3O_3)\cdot 2H_2O$ single crystal:
  $RbOH\cdot H_2O$ 7.23 g (0.06 mol)
  $LiOH\cdot H_2O$ 2.60 g (0.06 mol)
  $H_3C_3N_3O_3$ 7.74 g (0.06 mol)
  $H_2O$ 50 ml The specific operation steps were as follows: the above raw materials weighed according to the above amounts were put into a 100 ml beaker, to which was put a magnetic bar; the beaker was placed on a magnetic heating stirrer; the beaker was heated to 80° C. with stirring, and then cooled to 40° C. at a cooling rate of 1° C./hour. After cooling, the sample was washed with acetone to obtain $RbLi(HC_3N_3O_3)\cdot 2H_2O$ single crystal with a size of 2×2×5 mm.

Raw materials used for the preparation of $RbNa(HC_3N_3O_3)\cdot 2H_2O$ single crystal:
  NaOH 2.40 g (0.06 mol)
  $RbOH\cdot H_2O$ 7.23 g (0.06 mol)
  $H_3C_3N_3O_3$ 7.74 g (0.06 mol)
  $H_2O$ 50 ml The specific operation steps were as follows: the above raw materials weighed according to the above amounts were put into a 100 ml beaker, to which was put a magnetic bar; the beaker was placed on a magnetic heating stirrer; the beaker was heated to 80° C. with stirring, and then cooled to 10° C. at a cooling rate of 1° C./hour. After cooling, the sample was washed with acetone to obtain $RbNa(HC_3N_3O_3)\cdot 2H_2O$ single crystal with a size of 2×5×2 mm.

EXAMPLE 3

The $KLi(HC_3N_3O_3)\cdot 2H_2O$, $RbLi(HC_3N_3O_3)\cdot 2H_2O$ and $RbNa(HC_3N_3O_3)\cdot 2H_2O$ crystals obtained in Example 2 were processed, cut, oriented and polished, and then placed at the position 3 in the device shown in FIG. 1. At room temperature, using Q-switch Nd:YAG laser as input light source, with incident wavelength of 1064 nm, an obvious 532 nm frequency doubling green light output was observed, with output intensity about 2-3 times that of KDP under the equal conditions. Specifically, the output intensity of $KLi(HC_3N_3O_3)\cdot 2H_2O$ crystal was about 3 times that of KDP under the equal conditions, the output intensity of $RbLi(HC_3N_3O_3)\cdot 2H_2O$ crystal was about 2 times that of KDP under the equal conditions, and the output intensity of RbNa(HC$_3$N$_3$O$_3$)·2H$_2$O crystal was about 2 times that of KDP under the equal conditions.

The embodiments of the present invention have been described above. However, the present invention is not limited to the above embodiments. Any modification, equivalent replacement, improvement and the like made without departing from the spirit and principle of the present invention shall fall within the protection scope of the present invention.

The invention claimed is:

1. An alkali metal monohydrogen cyanurate compound having a formula of AM(HC$_3$N$_3$O$_3$)·nH$_2$O, wherein A and M are different and are independently selected from Li, Na, K, Rb, Cs, and Fr, and n is an integer of 0-10.

2. The compound of claim 1, wherein n is 2.

3. The compound of claim 1, selected from potassium lithium monohydrogen cyanurate dihydrate (KLi(HC$_3$N$_3$O$_3$)·2H$_2$O), rubidium lithium monohydrogen cyanurate dihydrate (RbLi(HC$_3$N$_3$O$_3$)·2H$_2$O), and rubidium sodium monohydrogen cyanurate dihydrate (RbNa(HC$_3$N$_3$O$_3$)·2H$_2$O).

4. The compound of claim 1, wherein the compound is a nonlinear optical crystal of potassium lithium monohydrogen cyanurate dihydrate, the chemical formula of which is KLi(HC$_3$N$_3$O$_3$)·2H$_2$O.

5. The compound of claim 1, wherein the compound is a nonlinear optical crystal of rubidium lithium monohydrogen cyanurate dihydrate, the chemical formula of which is RbLi(HC$_3$N$_3$O$_3$)·2H$_2$O.

6. The compound of claim 1, wherein the compound is a nonlinear optical crystal of rubidium sodium monohydrogen cyanurate dihydrate, the chemical formula of which is RbNa(HC$_3$N$_3$O$_3$)·2H$_2$O.

7. A method for preparing the compound of claim 1, comprising reacting AOH·xH$_2$O, MOH·yH$_2$O with H$_3$C$_3$N$_3$O$_3$ in a reaction liquid to obtain the alkali metal monohydrogen cyanurate compound, wherein x and y are, the same or different, independently 0 or more.

8. The method of claim 7, wherein a molar ratio of the AOH·xH$_2$O, MOH·yH$_2$O and H$_3$C$_3$N$_3$O$_3$ is (0.5-2.5):(0.5-2.5):1.

9. The method of claim 7, further comprising cooling the reaction liquid; and washing the obtained alkali metal monohydrogen cyanurate compound.

10. A method for frequency conversion of laser output, comprising passing a laser beam through an optical crystal made of the compound of claim 1.

11. An optical device comprising an optical crystal made of the compound of claim 1, wherein the optical device is a harmonic generator, an optical parametric amplifier, or an optical waveguide.

Figure 3:
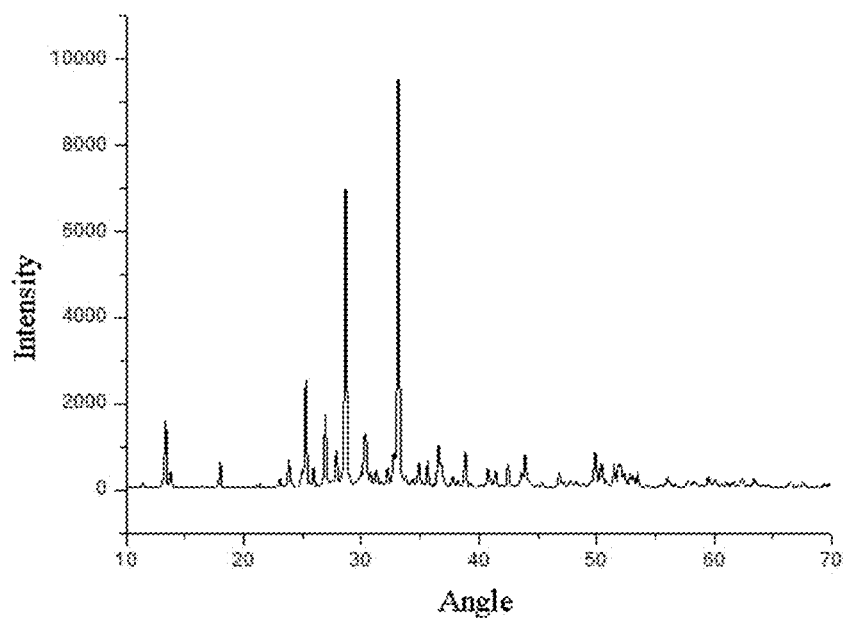
FIG. 3 is the X-ray diffraction pattern of KLHCY single crystal after grinding into powder.

12. The compound of claim 4, wherein the nonlinear optical crystal of potassium lithium monohydrogen cyanurate dihydrate has an X-ray powder diffraction pattern as shown in FIG. 3.

13. The compound of claim 4, wherein the nonlinear optical crystal of potassium lithium monohydrogen cyanurate dihydrate does not have a symmetry center, and belongs to an orthorhombic crystal system, having space group Pna2(1) and cell parameters a=15.387(6) Å, b=3.6524(16) Å, c=12.755(6) Å, α=β=γ=90°, Z=4, and a unit cell volume V=716.82 Å$^3$.

Figure 4:
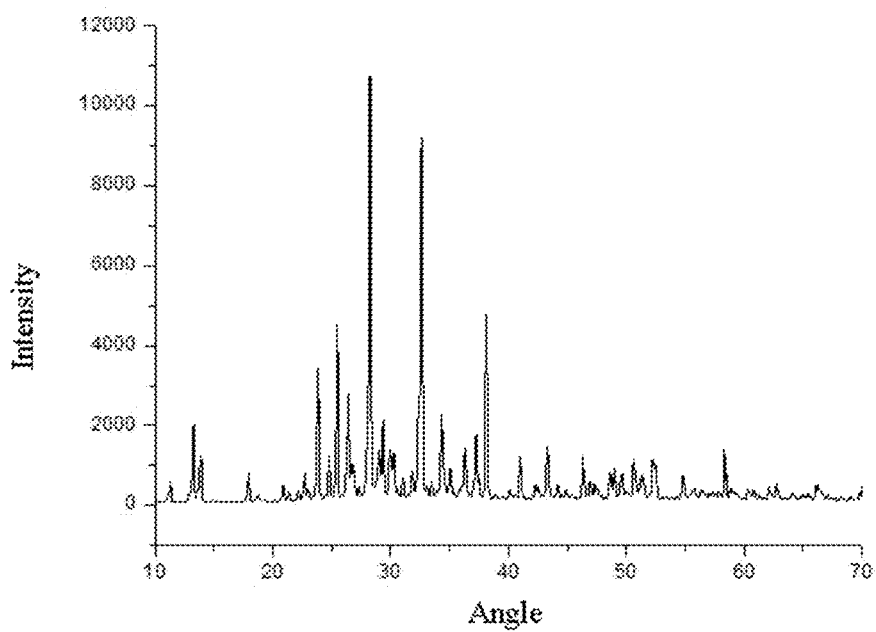
FIG. 4 is the X-ray diffraction pattern of RLHCY single crystal after grinding into powder.

14. The compound as claimed in claim 5, wherein the nonlinear optical crystal of rubidium lithium monohydrogen cyanurate dihydrate has an X-ray powder diffraction pattern as shown in FIG. 4.

15. The compound as claimed in claim 5, wherein the nonlinear optical crystal of rubidium lithium monohydrogen cyanurate dihydrate does not have a symmetry center, and belongs to an orthorhombic crystal system, having space group Pna2(1), cell parameters a=15.682(7) Å, b=3.7453(17) Å, c=12.768(6) Å, α=β=γ=90°, Z=4, and a unit cell volume V=749.9 Å$^3$.

Figure 5:
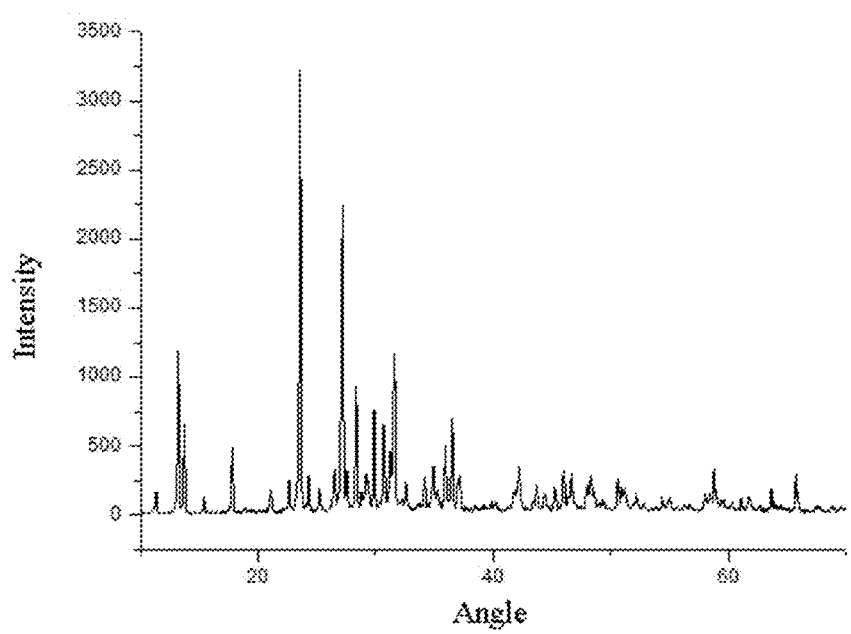
FIG. 5 is the X-ray diffraction pattern of RNHCY single crystal after grinding into powder.

16. The compound of claim 6, wherein the nonlinear optical crystal of rubidium sodium monohydrogen cyanurate dihydrate has an X-ray powder diffraction pattern as shown in FIG. 5.

17. The compound of claim 6, wherein the nonlinear optical crystal of rubidium sodium monohydrogen cyanurate dihydrate does not have a symmetry center, and belongs to an orthorhombic crystal system, having space group Pna2(1), cell parameters α=15.829(18) Å, b=3.964(5) Å, c=13.068(16) Å, α=β=γ=90°, Z=4, and a unit cell volume V=819.8 Å$^3$.

18. The method of claim 8, wherein the reaction is carried out in an organic solvent or an inorganic solvent; and/or the reaction is carried out at a temperature of 50-110° C.

19. The method of claim 9, wherein:
the cooling rate is in a range of 1-10° C./hour; and/or
the reaction liquid is cooled to 0-40° C.; and/or
the alkali metal monohydrogen cyanurate compound is washed with water, acetone, or a mixture thereof.

* * * * *